(12) United States Patent
Chmielewski et al.

(10) Patent No.: US 10,875,895 B2
(45) Date of Patent: Dec. 29, 2020

(54) ANTIBACTERIAL CELL-PENETRATING PEPTIDES

(71) Applicant: Purdue Research Foundation, West Lafayette, IN (US)

(72) Inventors: Jean Anne Chmielewski, Lafayette, IN (US); Mohamed Seleem, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 16/682,004

(22) Filed: Nov. 13, 2019

(65) Prior Publication Data

US 2020/0172579 A1 Jun. 4, 2020

Related U.S. Application Data

(60) Provisional application No. 62/915,683, filed on Oct. 16, 2019, provisional application No. 62/775,086, filed on Dec. 4, 2018.

(51) Int. Cl.
| | | |
|---|---|---|
| *C07K 9/00* | (2006.01) | |
| *A61P 31/04* | (2006.01) | |
| *A61K 47/55* | (2017.01) | |
| *A61K 31/7036* | (2006.01) | |
| *A61K 49/00* | (2006.01) | |
| *A61K 38/00* | (2006.01) | |
| *A61K 45/06* | (2006.01) | |

(52) U.S. Cl.
CPC .......... *C07K 9/008* (2013.01); *A61K 31/7036* (2013.01); *A61K 47/552* (2017.08); *A61K 49/0056* (2013.01); *A61P 31/04* (2018.01); *A61K 38/00* (2013.01); *A61K 45/06* (2013.01)

(58) Field of Classification Search
CPC .............. A61K 47/552; A61K 31/7036; A61K 31/395; A61K 47/65; A61K 47/61; A61K 31/7048

See application file for complete search history.

(56) References Cited

U.S. PATENT DOCUMENTS

| | | | |
|---|---|---|---|
| 9,533,975 B2 | 1/2017 | Chmielewski | |
| 10,265,408 B2 * | 4/2019 | Chmielewski | ....... A61K 31/395 |

OTHER PUBLICATIONS

Anna Brezden, et al., Dual targeting of intracellular pathogenic bacteria with a cleavable conjugate of kanamycin and an antibacterial cell-penetrating peptide, J. Am. Chem. Soc., 2016, 138, 10945-10949.

Kuriakose J., et al., Targeting intracellular pathogenic bacteria with unnatural proline-rich peptides: coupling antibacterial activity with macrophage penetration, Angew. Chem. Int. Ed. 2013, 52 (37), 9664.

* cited by examiner

*Primary Examiner* — Sudhakar Katakam
(74) *Attorney, Agent, or Firm* — Purdue Research Foundation; Zhigang Rao

(57) ABSTRACT

The present disclosure relates to novel antibacterial cell-penetrating peptides and derivatives, and methods to make and use the novel antibacterial cell-penetrating peptides and derivatives. The novel antibacterial cell-penetrating peptides of the present invention with shorter linker between a pyrrolidine ring and a guanidine group provide unexpectedly higher potency against a broader scope of bacterial.

15 Claims, No Drawings

ANTIBACTERIAL CELL-PENETRATING PEPTIDES

CROSS-REFERENCE TO RELATED APPLICATION

This application claims the benefits of U.S. Provisional Application Ser. No. 62/775,086 filed Dec. 4, 2018, and 62/915,683 filed Oct. 16, 2019, the contents of which are incorporated herein entirely.

GOVERNMENT RIGHTS

This invention was made with government support under CHE1412902 awarded by the National Science Foundation. The United States government has certain rights in the invention.

TECHNICAL FIELD

The present disclosure relates to novel antibacterial cell-penetrating peptides and derivatives, and methods to make and use the novel antibacterial cell-penetrating peptides and derivatives.

BACKGROUND

This section introduces aspects that may help facilitate a better understanding of the disclosure. Accordingly, these statements are to be read in this light and are not to be understood as admissions about what is or is not prior art.

A significant challenge in the development of effective antibacterial agents arises from bacterial pathogens, including *Mycobacterium tuberculosis, Salmonella, Brucella, Listeria, Shigella*, and methicillin-resistant *S. aureus* (MRSA), that have evolved to inhabit mammalian cells, such as phagocytic macrophages. Moreover, most of the bacterial bioterrorism agents monitored by the U.S. Centers for Disease Control and Prevention are intracellular pathogens, such as multidrug-resistant *Mycobacterium* (tuberculosis, TB), *Yersinia pestis* (plague), *Salmonella* species (salmonellosis), *Fancisella tularensis* (tularemia), *Brucella* species (brucellosis), *Chlamydia psittaci* (psittacosis), *Coxiella burnetii* (Q fever), *Rickettsia prowazekii* (typhus fever), *Burkholderia mallei* (glanders) and *Burkholderia pseudomallei* (melioidosis). Within these intracellular safe havens the bacteria reproduce and form a repository, often causing chronic infections. Infected patients become life-long carriers of the pathogens, and chronically suffer from the infection or die from invasive forms of the pathogen. For example, in 2013, 9 million people around the world became sick with TB disease and there are an estimated 1.5 million TB-related deaths annually. Also, *Salmonella* infection affects >100 million people worldwide, accounting for 370,000 deaths annually. In addition, some intracellular pathogens are capable of switching to a dormant stage of growth, thus enabling long-term colonization of the host and relapses, even after prolonged antibiotic therapy.

Whereas these pathogenic bacteria are internalized within macrophages, many of the commonly used classes of antibiotics, such as aminoglycosides, glycopeptides and macrolides, do not effectively accumulate within these cells. This is due, in part, to inefficient membrane penetration and susceptibility to drug efflux transporters. As such, the therapeutic value of many antibiotics against intracellular bacteria is severely limited. For instance, it is generally accepted that aminoglycosides have poor internalization within macrophages, with activity developing slowly because of the low rate of uptake. For instance, kanamycin has demonstrated only about 50% reduction in *M. tuberculosis* levels within THP-1 macrophages after 10 days.

One approach to target intracellular pathogenic bacteria uses delivery vehicles, such as liposomes and micro/nanoparticles, that are loaded with antibiotics. While these vehicles have demonstrated cellular delivery of antibiotics and reduction in intracellular bacteria levels, they suffer from instability to biological fluids and difficulties in drug loading. Recently a non-cleavable conjugate of methotrexate and a short cell penetrating peptide was demonstrated to target intracellular *Listeria*, whereas a cell penetrating peptide with intrinsic antimicrobial activity, Fl-$P_R P_R P_L$-4 (or P14LRR), was shown to target intracellular *Salmonella* and *Brucella*. See Kuriakose, J. et al., Targeting intracellular pathogenic bacteria with unnatural proline-rich peptides: coupling antibacterial activity with macrophage penetration, *Angew. Chem. Int. Ed.* 2013, 52 (37), 9664. This latter peptide forms a cationic amphiphilic polyproline helix and is a non-membrane lytic, broad spectrum antibiotic. Brezden, A. et al. reported a cell-permeable, dual antimicrobial agent that reversibly links the antibacterial P14LRR with the aminoglycoside antibiotic kanamycin to achieve an agent with synergistic activity against intracellular pathogenic bacteria. See Brezden, A. et al., Dual Targeting of Intracellular Pathogenic Bacteria with a Cleavable Conjugate of Kanamycin and an Antibacterial Cell-Penetrating Peptide, *Journal of the American Chemical Society*, 2016 38 (34), 10945-10949.

While these reported peptide-based agents display a good reduction in intracellular bacteria, much more potent agents are needed to effectively eradicate pathogenic bacteria from mammalian cells.

SUMMARY

The present invention provides novel antibacterial cell-penetrating peptides and derivatives, and methods to make and use the novel antibacterial cell-penetrating peptides and derivatives. Specifically, the novel cell-penetrating peptides of the present disclosure are represented in the Formula I below:

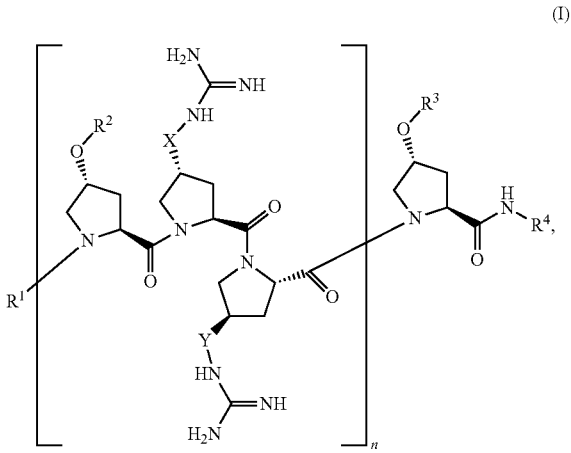

(I)

or a stereoisomer, tautomer, solvate, pharmaceutically acceptable salt, or derivative thereof, wherein:

$R^1$ is H, an optionally substituted straight, branched or cyclic alkyl or acyl, an optionally substituted aryl or aroyl, an optionally substituted heteroaryl or heteroaroyl, an amino acid moiety, a dye moiety, a fluorophore moiety, a pharmaceutical conjugating agent moiety, an antibiotic moiety, or

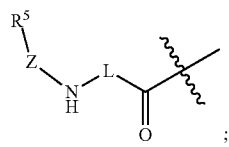

$R^2$ and $R^3$ are each independently H, a $C_1$-$C_8$ branched or unbranched alkyl chain, a $C_3$-$C_8$ cyclic alkyl, an optionally substituted aryl, or an optionally substituted heteroaryl;

$R^4$ is H, a $C_1$-$C_8$ branched or unbranched alkyl chain, or a $C_3$-$C_8$ cyclic alkyl, an optionally substituted aryl, or an optionally substituted heteroaryl;

$R^5$ is H, a dye moiety, a fluorophore moiety, a pharmaceutical conjugating agent moiety, or an antibiotic moiety;

L is $C_1$-$C_8$ branched or unbranched alkyl chain, or a $C_3$-$C_8$ cyclic alkyl;

X and Y are each independently a bond, or a $C_1$-$C_3$ linker, wherein one of the carbon of the $C_1$-$C_3$ linker is optionally replaced with a heteroatom selected from the group consisting of N, O, and S;

Z is a bond, or a linker comprising an optionally substituted straight, branched or cyclic alkyl, an amide group, a carbonyl group, a heteroatom selected from the group consisting of N, O, and S, a disulfide bond (S—S bond), or any combination thereof; and n is 2-8.

In one embodiment, the present disclosure provides methods for treating a patient, either mammal or animal, having a microbial infection with the presently disclosed novel antibiotics and an antibacterial cell-penetrating peptide, or a stereoisomer, tautomer, solvate, pharmaceutically acceptable salt, or derivative thereof.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In the present disclosure the term "about" can allow for a degree of variability in a value or range, for example, within 10%, within 5%, or within 1% of a stated value or of a stated limit of a range.

As used herein, the term "salts" and/or "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

As used herein, the term "nitrogen-protecting group" in the present disclosure may be any functional group that can make the amine nitrogen to be protected as any form of carbamate, benzyl amine, amide, thioamide, sulfonamide, urea, or thiourea. The nitrogen-protecting group may include but is not limited to benzoyl, benzyloxycarbonyl, t-butoxycarbonyl (Boc), benzene sulfonyl, toluene sulfonyl, benzyl, benzhydryl, trityl, acetyl, fluorenylmethyloxycarbonyl protecting group (Fmoc), or trifluoroacetyl.

As used herein, a fluorophore (or fluorochrome, similarly to a chromophore) is a fluorescent chemical compound that can re-emit light upon light excitation. Fluorophores typically contain several combined aromatic groups, or planar or cyclic molecules with several π bonds. A fluorophore for the present disclosure may be but is not limited to fluorescein, rhodamine, Oregon green, eosin, and Texas red, cyanine, indocarbocyanine, oxacarbocyanine, thiacarbocyanine, merocyanine, squaraines, SeTau, Square dyes, naphthalene, or derivatives thereof.

As used herein, the term "dye" is a colored substance that has an affinity to the substrate to which it is being applied. A dye may be a fluorophore material.

As used herein, the term "antibiotics" refers to any anti-bacterial antibiotics, which are antibiotics that do not have activity against viruses, fungi and other non-bacterial microbes. The anti-bacterial antibiotics include bactericidal antibiotics, which destroy bacteria, and bacteriostatic antibiotics which prevent bacteria from multiplying. The anti-bacterial antibiotics further include "narrow-spectrum" antibiotics which target particular types of bacteria, such as Gram negative or Gram-positive bacteria, and broad spectrum antibiotics which affect a wide range of bacteria. Likewise, the anti-bacterial antibiotics include antibiotics for ingestion as well as antibiotics for intravenous administration which are often used to treat serious infections such as deep-seeded systemic infections, and antibiotics for topical and inhalation administration. The anti-bacterial antibiotics comprise antibiotics within the following presently recognized classes: aminoglycoside antibiotics, Ansamycins, Beta-lactam antibiotics (including the carbacephem, carbapenems, cephalosporins (first, second, third and fourth generations), monobactams and penicillins, Glycopeptides, Macrolides, lincosamides, Polypeptides, Quinolones, Sulphonamides, Tetracyclines, Cyclic lipopeptides, Glycylcyclines, Oxazolidinones, diaminopyrimidines, Nitrofurans, Rifamycins, antibiotic peptides, amphenicols, nitroimidazoles, streptogramins and phosphomycins.

As used herein, the particular term "aminoglycoside antibiotics" refers to a medicinal and bacteriologic category of traditional antibacterial therapeutic agents that inhibit protein synthesis and contain as a portion of the molecule an amino-modified glycoside (sugar). The term can also refer more generally to any organic molecule that contains amino sugar substructures. Aminoglycoside antibiotics may include but is not limited to Gentamicin, Streptomycin, Kanamycin, Fradiomyctn, Paromomycin, Tobramycin, Netilmicin, Amikacin, Neomycin, Ribostamycin, Dibekacin, Sisomicin, Isepamicin, Bekanamycin, Astromicin, Plazomicin, or any derivative thereof.

As used herein, the term "antibiotic moiety" as referred in a chemical structure refers to the structure of an antibiotic agent that is chemically linked to the structure of another chemical or partial structure of another chemical, through a chemical functional groups such as an ester group, an amide group or an acyl amide group through the hydroxyl, amino or amide group of the antibiotic agent.

As used herein, the term "pharmaceutical conjugating agent moiety" refers to the partial structure of any suitable pharmaceutical agent such as a FDA approved drug that can be chemically linked to the structure of another chemical or partial structure of another chemical, through a chemical functional groups.

The term "cleavable" means that the compound of the present disclosure can be cleaved from a disulfide bond (—S—S—).

Comparing with previously disclosed antibacterial cell-penetrating peptides, the present disclosure provides novel antibacterial cell-penetrating peptides that have shorter linker between a pyrrolidine ring and a guanidine group. Such modified peptides with shorter linkers, such as Example 1, provided unexpectedly higher potency against a broader scope of bacterial (see Table 1 of the present disclosure).

The present invention provides novel cleavable conjugated cell penetrating peptides. Accordingly, the present invention provides a compound of Formula I:

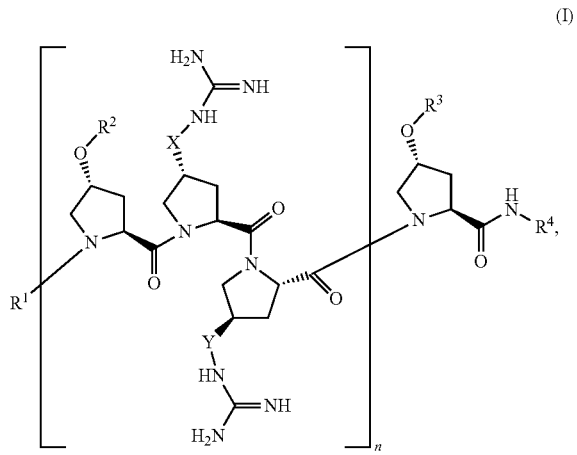

(I)

or a stereoisomer, tautomer, solvate, pharmaceutically acceptable salt, or derivative thereof, wherein:

$R^1$ is H, an optionally substituted straight, branched or cyclic alkyl or acyl, an optionally substituted aryl or aroyl, an optionally substituted heteroaryl or heteroaroyl, an amino acid moiety, a dye moiety, a fluorophore moiety, a pharmaceutical conjugating agent moiety, an antibiotic moiety, or

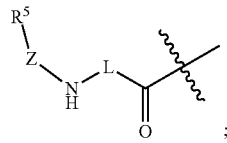

;

$R^2$ and $R^3$ are each independently H, a $C_1$-$C_8$ branched or unbranched alkyl chain, a $C_3$-$C_8$ cyclic alkyl, an optionally substituted aryl, or an optionally substituted heteroaryl;

$R^4$ is H, a $C_1$-$C_8$ branched or unbranched alkyl chain, or a $C_3$-$C_8$ cyclic alkyl, an optionally substituted aryl, or an optionally substituted heteroaryl;

$R^5$ is H, a dye moiety, fluorophore moiety, a pharmaceutical conjugating agent moiety, or an antibiotic moiety;

L is $C_1$-$C_8$ branched or unbranched alkyl chain, or a $C_3$-$C_8$ cyclic alkyl;

X and Y are each independently a bond, or a $C_1$-$C_3$ linker, wherein one of the carbon of the $C_1$-$C_3$ linker is optionally replaced with a heteroatom selected from the group consisting of N, O, and S;

Z is a bond, or a linker comprising an optionally substituted straight, branched or cyclic alkyl, an amide group, a carbonyl group, a heteroatom selected from the group consisting of N, O, and S, a disulfide bond (S—S bond), or any combination thereof; and n is 2-8.

In one embodiment, the present invention provides a compound of Formula I, wherein $R^1$ and/or $R^5$ represents the moiety of an aminoglycoside antibiotics or any derivative thereof.

In one embodiment, the present invention provides a compound of Formula I, wherein $R^1$ and/or $R^5$ represents an aminoglycoside antibiotics moiety, wherein the aminoglycoside antibiotics is selected from the group consisting of Gentamicin, Streptomycin, Kanamycin, Fradiomyctn, Paromomycin, Tobramycin, Netilmicin, Amikacin, Neomycin, Ribostamycin, Dibekacin, Sisomicin, Isepamicin, Bekanamycin, Astromicin, Plazomicin, and any derivative thereof.

In one embodiment, the present invention provides a compound of Formula I, wherein $R^1$ and/or $R^5$ represents Vancomycin, Linezolid, Erythromycin, Eperezolid, or any derivative thereof.

In one embodiment, the present invention provides a compound of Formula I, wherein $R^1$ and/or $R^5$ represents an antibiotics moiety of an antibiotics, and wherein the antibiotics is selected from the group consisting of Gentamicin, Streptomycin, Kanamycin, Fradiomyctn, Paromomycin, Tobramycin, Netilmicin, Amikacin, Neomycin, Ribostamycin, Dibekacin, Sisomicin, Isepamicin, Bekanamycin, Astromicin, Plazomicin, Vancomycin, Linezolid, Erythromycin, Eperezolid, and any derivative thereof.

In one embodiment, the present invention provides a compound of Formula I, wherein $R^2$ and $R^3$ are each independently $C_1$-$C_4$ branched or unbranched alkyl chain.

In one embodiment, the present invention provides a compound of Formula I, wherein $R^2$ and $R^3$ are isobutyl group.

In one embodiment, the present invention provides a compound of Formula I, wherein $R^4$ is hydrogen.

In one embodiment, the present invention provides a compound of Formula I, wherein L is $C_1$-$C_4$ branched or unbranched alkyl chain. In one aspect, L is a methylene group.

In one embodiment, the present invention provides a compound of Formula I, wherein $R^1$ and/or $R^5$ represents an antibiotics moiety of an antibiotics, and wherein the antibiotics is selected from the group consisting of Gentamicin, Streptomycin, Kanamycin, Fradiomyctn, Paromomycin, Tobramycin, Netilmicin, Amikacin, Neomycin, Ribostamycin, Dibekacin, Sisomicin, Isepamicin, Bekanamycin, Astromicin, Plazomicin, Vancomycin, Linezolid, Erythromycin, Eperezolid, and any derivative thereof; $R^2$ and $R^3$ are isobutyl group; $R^4$ is hydrogen; and L is —(CH$_2$)—; X and Y are each independently a bond; and n is 4.

In one embodiment, the present invention provides a compound of Formula I, wherein $R^1$ and/or $R^5$ represents an aminoglycoside antibiotics moiety of an antibiotics, and wherein the antibiotics is selected from the group consisting of Gentamicin, Kanamycin, Tobramycin, Amikacin, Neomycin, Plazomicin, and any derivative thereof; $R^2$ and $R^3$ are isobutyl group; $R^4$ is hydrogen; L is —$(CH_2)$—; X and Y are each independently a bond; and n is 4.

In one embodiment, the present invention provides a compound of Formula I, wherein $R^1$ and/or $R^5$ represents an aminoglycoside antibiotics moiety, and the aminoglycoside antibiotics is Kanamycin or any derivative thereof; $R^2$ and $R^3$ are isobutyl group; $R^4$ is hydrogen; L is —$(CH_2)$—; X and Y are each independently a bond; and n is 4.

In one embodiment, the present invention provides a compound of Formula I, wherein $R^5$ is a fluorescein moiety, $R^2$ and $R^3$ are isobutyl group; $R^4$ is hydrogen; L is —$(CH_2)$—; X and Y are a bond; Z is a carbonyl group; and n is 4 (Formula II):

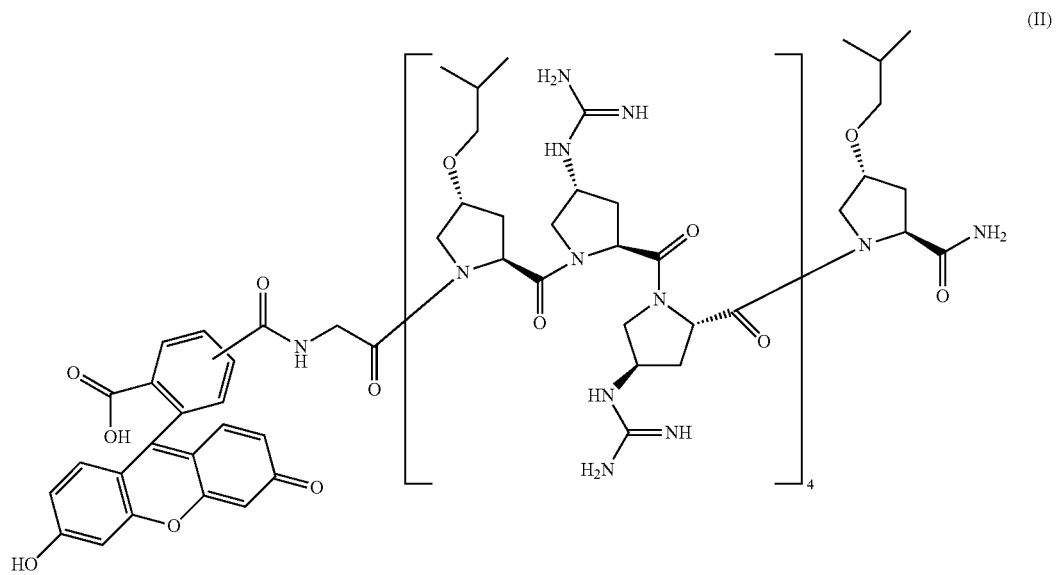

(II)

In one embodiment, the present invention provides a compound selected from the group consisting of:

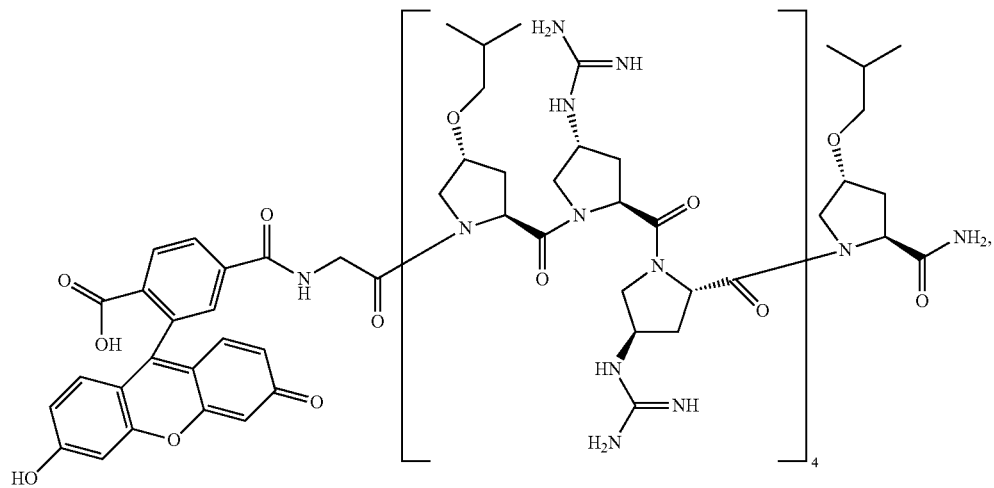

-continued
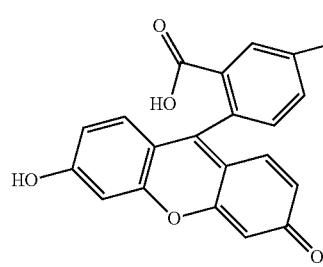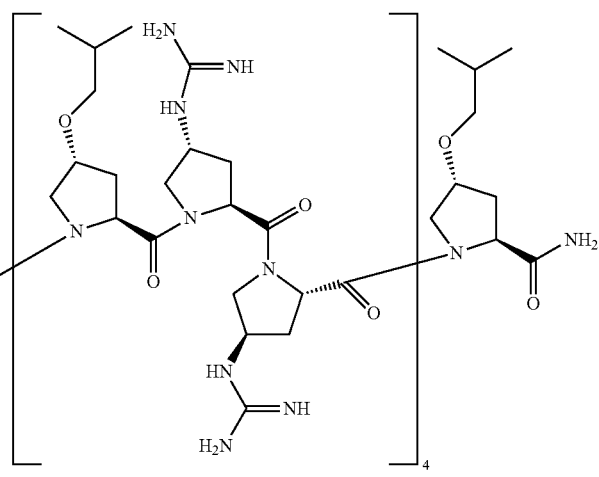
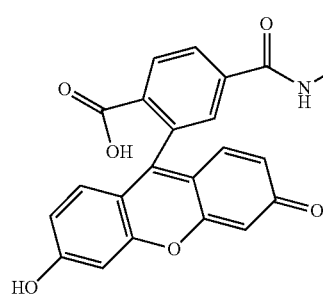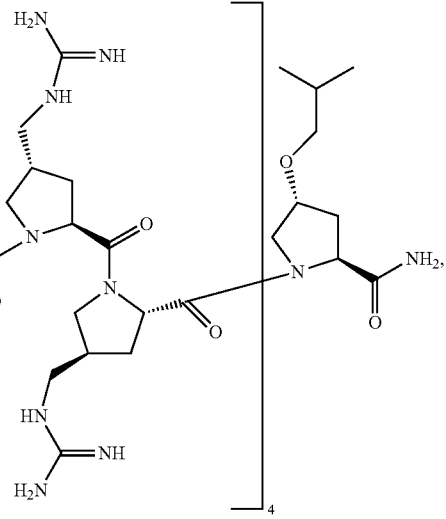
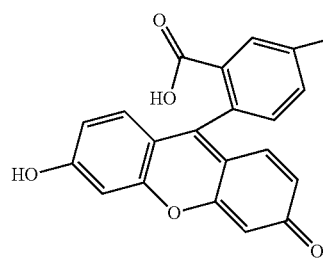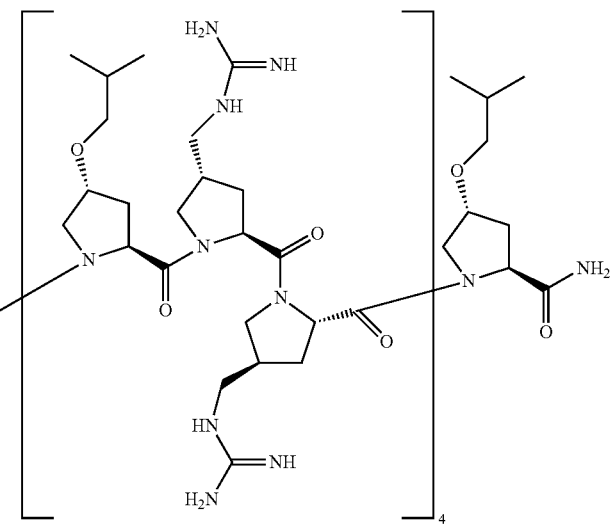

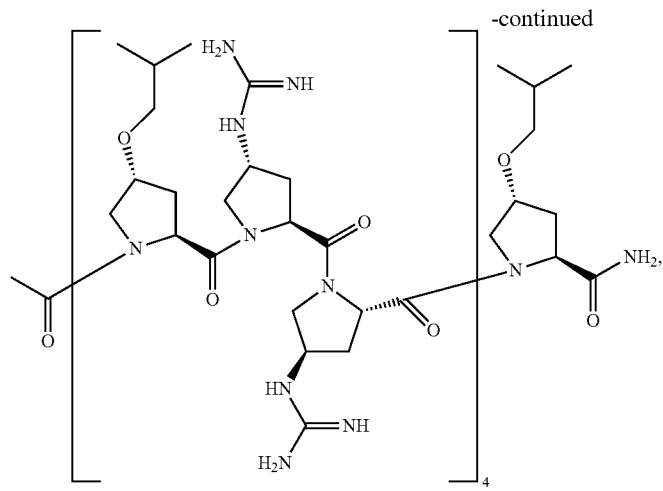

a stereoisomer, tautomer, solvate, pharmaceutically acceptable salt, derivative, and prodrug thereof.

In one embodiment, the present invention provides a method for treating a patient, either mammal or animal, having a microbial infection with any compound of Formula (I), or a stereoisomer, tautomer, solvate, pharmaceutically acceptable salt, or derivative thereof. In one aspect, the compound of Formula (I) is used for inhibiting the formation of a biofilm. In one aspect, the compound of Formula (I) is used for inhibiting the growth of an established biofilm. In one aspect, the compound of Formula (I) is used for anti-inflammatory purpose. In one aspect, the method comprises using a compound selected from the group consisting of:

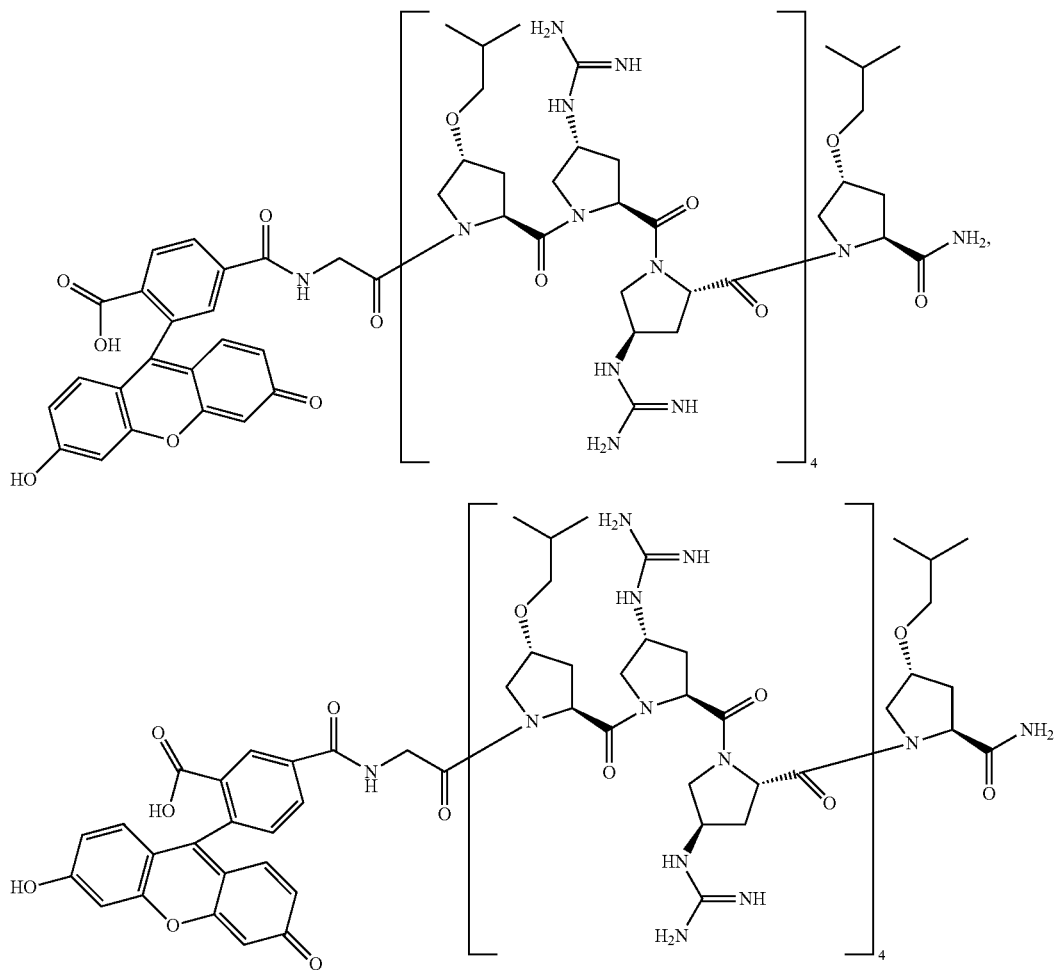

-continued
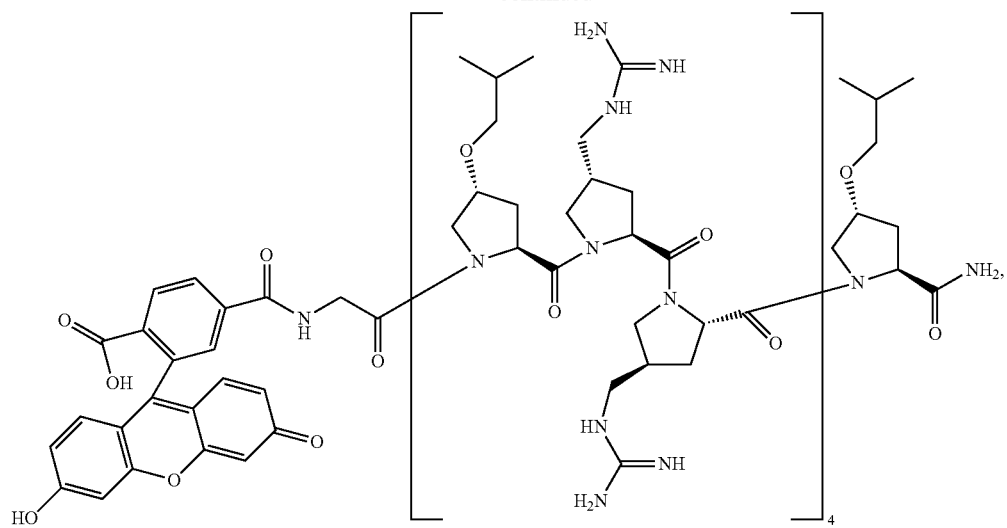
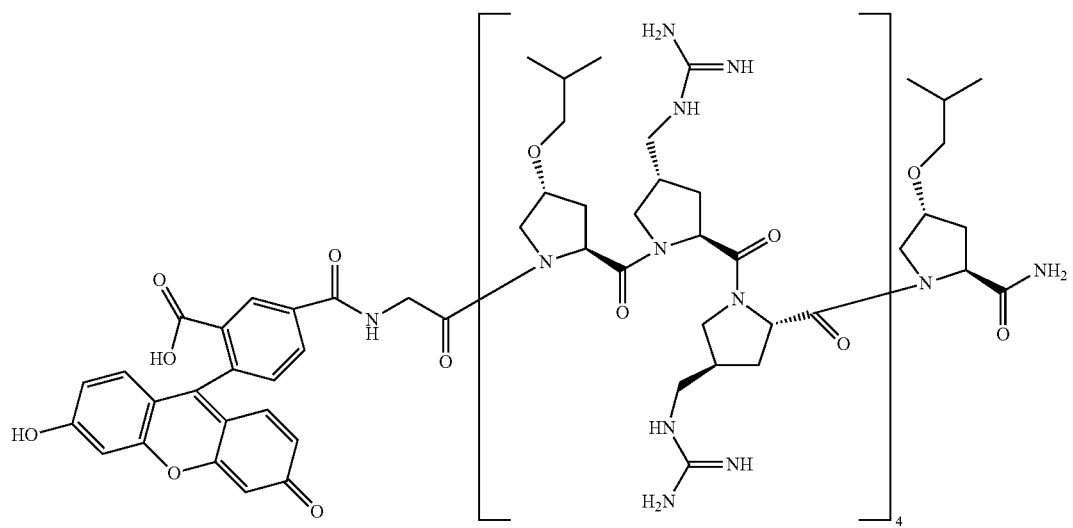
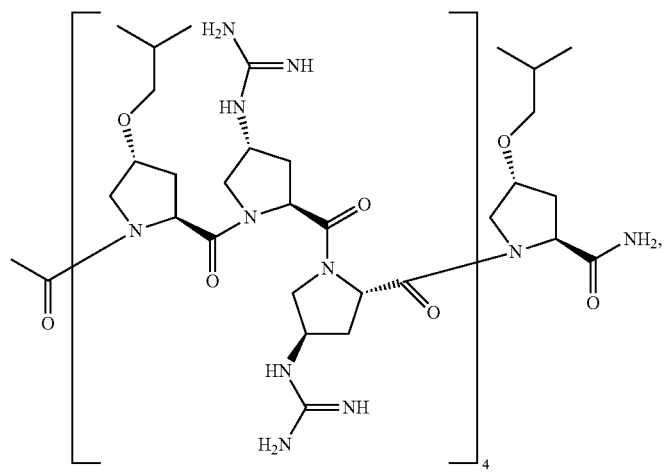

a stereoisomer, tautomer, solvate, pharmaceutically acceptable salt, derivative, and prodrug thereof.
EXPERIMENTAL SECTION
Synthesis of Example 1
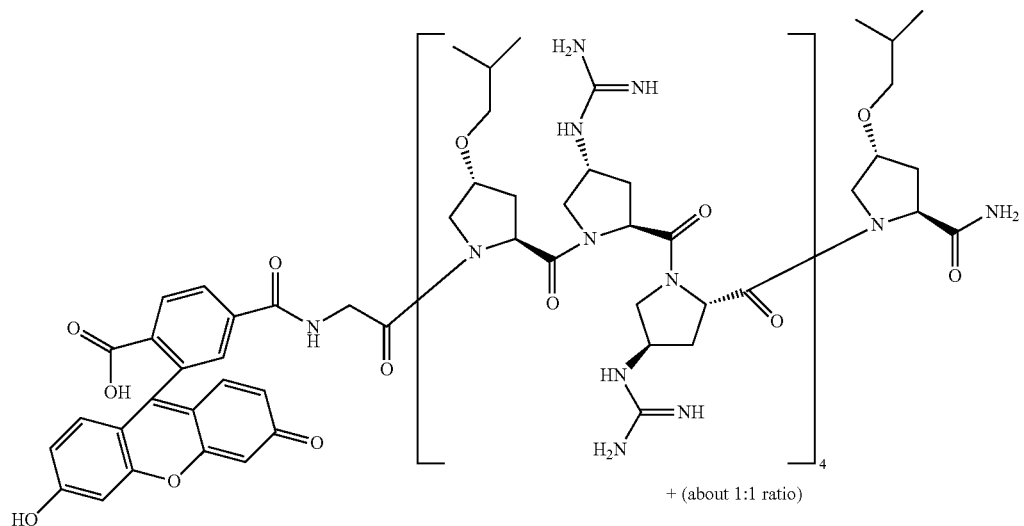
+ (about 1:1 ratio)
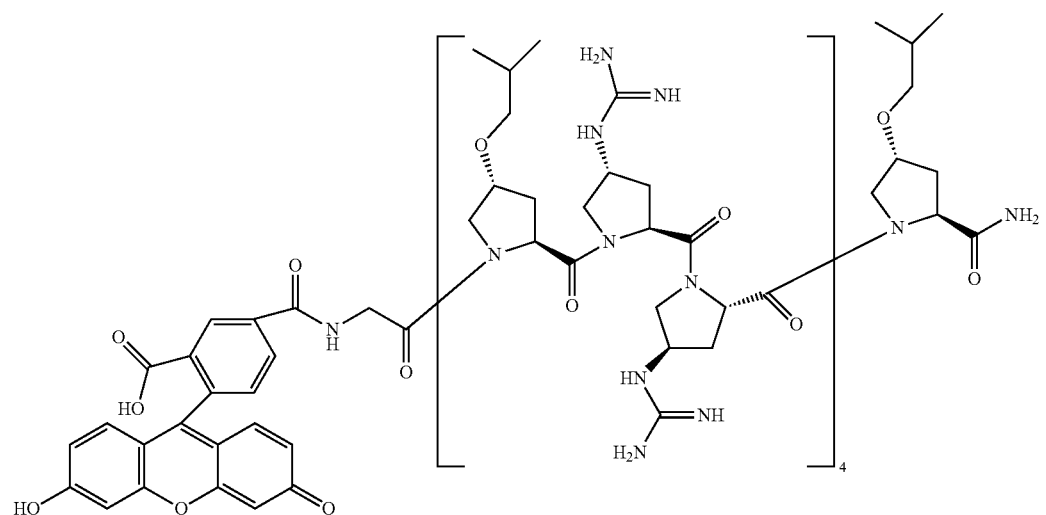

Example 1

About 1:1 Mixture Originated from the about 1:1 Mixture of 5-(and 6-)Carboxyfluorescein

Step 1: Fmoc-GAP(Boc)₂ (2) Synthesis

Scheme 1: Synthesis of Fmoc-GAP(Boc)₂ (2)

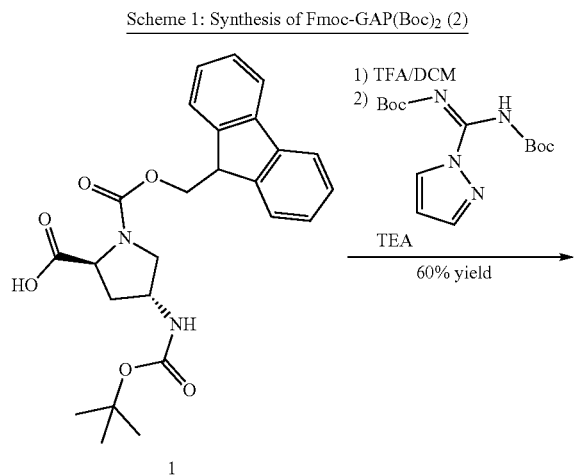

To Fmoc-L-Pro(4-NHBoc)-OH(2S,4R) (1) (200 mg, 0.44 mmol) in a 25 mL round bottom flask with a stir bar was added a triflouroacetic acid (TFA) and dichloromethane (DCM) solution (1:1, 2 mL). The reaction was stirred for 3 h at room temperature. The TFA/DCM solution was removed in vacuo and dried under high vacuum for 12 h. The residue was solubilized in DCM (2 mL) with sonication and N,N'-di-tert-butoxycarbonyl-1H-pyrazole-1 (150.9 mg, 0.49 mmol) was added to the reaction flask followed by triethylamine (TEA) (249 µL, 1.77 mmol). The resulting solution was stirred for 12 h at room temperature. The reaction mixture was extracted with a saturated sodium bicarbonate solution (3×). Followed by extraction with brine (2×). The organic layer was dried over sodium sulfate and the organic solvent was removed in vacuo. The crude material was purified by flash chromatography on silica gel with an eluent composed of 93% DCM and 7% methanol (MeOH). The desired fractions were collected and the solvent was removed in vacuo to yield a white solid, Fmoc-GAP(Boc)₂ (2) in 60% yield. MW: 594, ESI⁺MS: 595 m/z (M+H⁺).

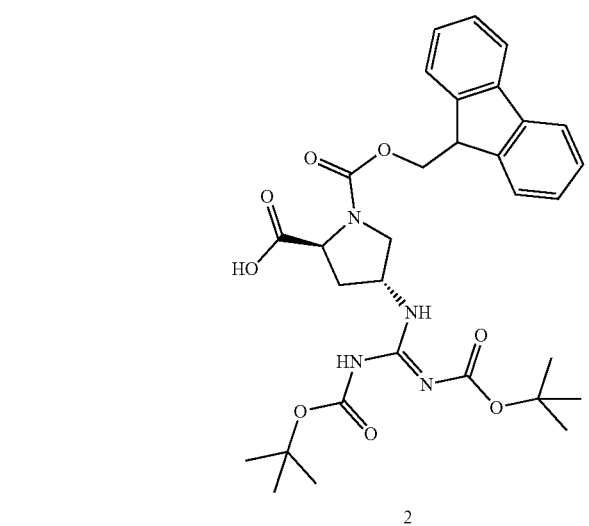

Step 2: P14-GAP Peptide Synthesis

To a 10 mL peptide synthesis flask was added Rink-Amide ChemMatrix resin (50 mg, 0.24 mmol/g loading). The resin was washed with dimethylformamide (DMF) (2×, about 4 mL each). In a 13×100 mm culture tube amino acid, Fmoc-P$_L$, (Compound 3, FIG. 1, JACS, 2005, 127, 11798-11803) (24.6 mg, 0.06 mmol) was activated with hexafluorophosphate azabenzotriazole tetramethyl uronium (HATU) (22.8 mg, 0.24 mmol) and diisopropylethylamine (DIEA) (20.9 µL, 0.12 mmol) in DMF (4 mL) with sonication for 10 min. The resulting solution was added to the peptide synthesis flask, and the flask was agitated for 4 h. The solution was drained from the synthesis flask and the resin was washed sequentially with DMF, DCM, MeOH, DCM and DMF (2×, about 4 mL each). Piperidine in DMF (20%, 4 mL) was added to the reaction flask, and the flask was agitated for 30 min. The piperidine was drained and the resin was washed sequentially with DMF, DCM, MeOH, DCM and DMF (2×, about 4 mL each). Next, amino acid Fmoc-GAP(Boc)₂ (Compound 2, FIG. 1) (35.7 mg, 0.06 mmol) was activated with HATU (22.8 mg, 0.24 mmol) and DIEA (20.9 µL, 0.12 mmol) in DMF (4 mL) in a 13×100 mm culture tube with sonication for 10 min. The resulting solution was added to the peptide synthesis flask, and the flask was agitated for 4 h. The solution was drained from the synthesis flask and the resin was washed sequentially with DMF, DCM, MeOH, DCM and DMF (2×, about 4 mL each). Piperidine in DMF (20%, 4 mL) was added to the reaction flask, and the flask was agitated for 30 min. The piperidine was drained and the resin was washed sequentially with DMF, DCM, MeOH, DCM and DMF (2×, about 4 mL each). This procedure was repeated to until the desired peptide sequence was synthesized ending with P$_L$ as the last amino acid. Commercially available Fmoc-Glycine (Compound 4, FIG. 1) (21.39 mg, 0.072 mmol) was activated with HATU (27.4 mg, 0.072 mmol) and DIEA (25 µL, 0.144 mmol) in DMF (4 mL) in a 13×100 mm culture tube with sonication for 10 min. The resulting solution was added to the peptide synthesis flask, and the flask was agitated for 3 h. The solution was drained from the synthesis flask and the resin was washed sequentially with DMF, DCM, MeOH, DCM and DMF (2×, about 4 mL each). Piperidine in DMF (20%, 4 mL) was added to the reaction flask, and the flask was agitated for 30 min. The piperidine was drained and the resin was washed sequentially with DMF, DCM, MeOH, DCM and DMF (2×, about 4 mL each). Finally, commercially available NHS-Fluorescein (Compound 5, a 1:1 mixture of 5-(and 6-)carboxyfluorescein) (12.49 mg, 0.026 mmol) dissolved in DMF (4 mL) with added DIEA (8.3 µL, 0.048 mmol) was added the reaction flask which was protected from light with foil. The flask was agitated for 24 h. The solvent was drained from the reaction flask and the resin was washed sequentially with DMF, DCM, MeOH, DCM (2×, about 4 mL each) followed by drying under high vacuum for 2 h.

Scheme 2: Reagent compounds 2-5 for P14-GAP peptide synthesis

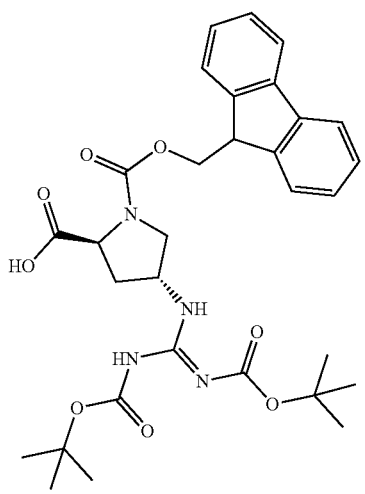

Fmoc-GAP(Boc)2

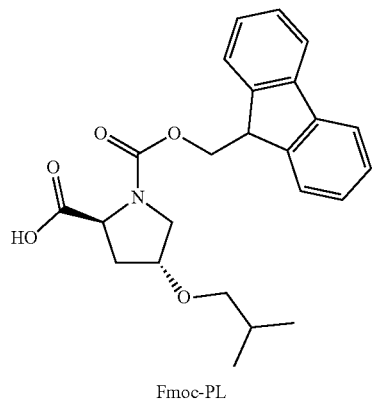

Fmoc-PL

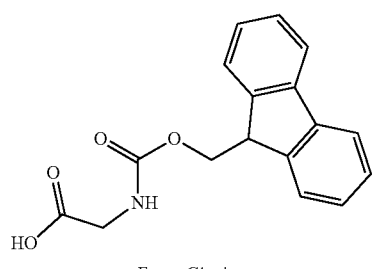

Fmoc-Glycine

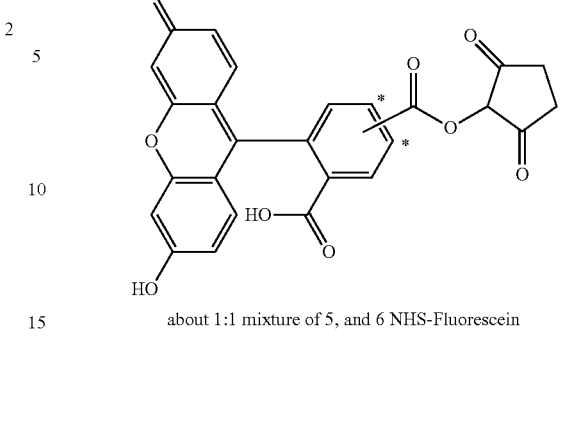

about 1:1 mixture of 5, and 6 NHS-Fluorescein

Step 3: Cleavage and Purification of P14-GAP Peptide

A TFA cocktail composed of TFA, triisopropylsilyl (TIPS), and water (95:2.5:2.5, 10 mL) was added to the peptide synthesis flask. The flask was agitated for 2 h. The solution was drained into a 50 mL centrifuge tube, the resin was rinsed with DCM (5 mL) and the wash was added to the same centrifuge tube. The solvent was removed in vacuo, the crude peptide was precipitated using cold diethyl ether (25 mL) and the tube was placed in a −80° C. freezer overnight. The precipitate was collected by centrifugation at 3500 rpm and the supernatant was decanted. The resulting precipitate was dissolved in water and purified using reverse phase high performance liquid chromatography (RP-HPLC) using a C18 semi preparative column. The eluent was composed of solvent A (acetonitrile with 0.1% TFA) and solvent B (water with 0.1% TFA) at a gradient of 15%-65% eluent A, at a flow rate of 12 mL/min, and UV detection at 214 nm and 254 nm. Fractions of the desired peptide were combined and lyophilized to obtain Fl P14-GAP Example 1 as a yellow solid (about 1:1 mixture originated from the about 1:1 mixture of 5-(and 6-)carboxyfluorescein). Analysis of the purity of the peptide was achieved by analytical RP-HPLC using a C18 analytical column, a flow rate of 1.2 mL/min, and UV detection at 214 nm and 254 nm; a purity of >95% was obtained. Characterization was achieved using matrix assisted laser desorption ionization—time of flight (MALDI-TOF) mass spectrometry. MW: 2510, MALDI-TOF+MS: 2510 m/z.

Synthesis of Example 2 and 3
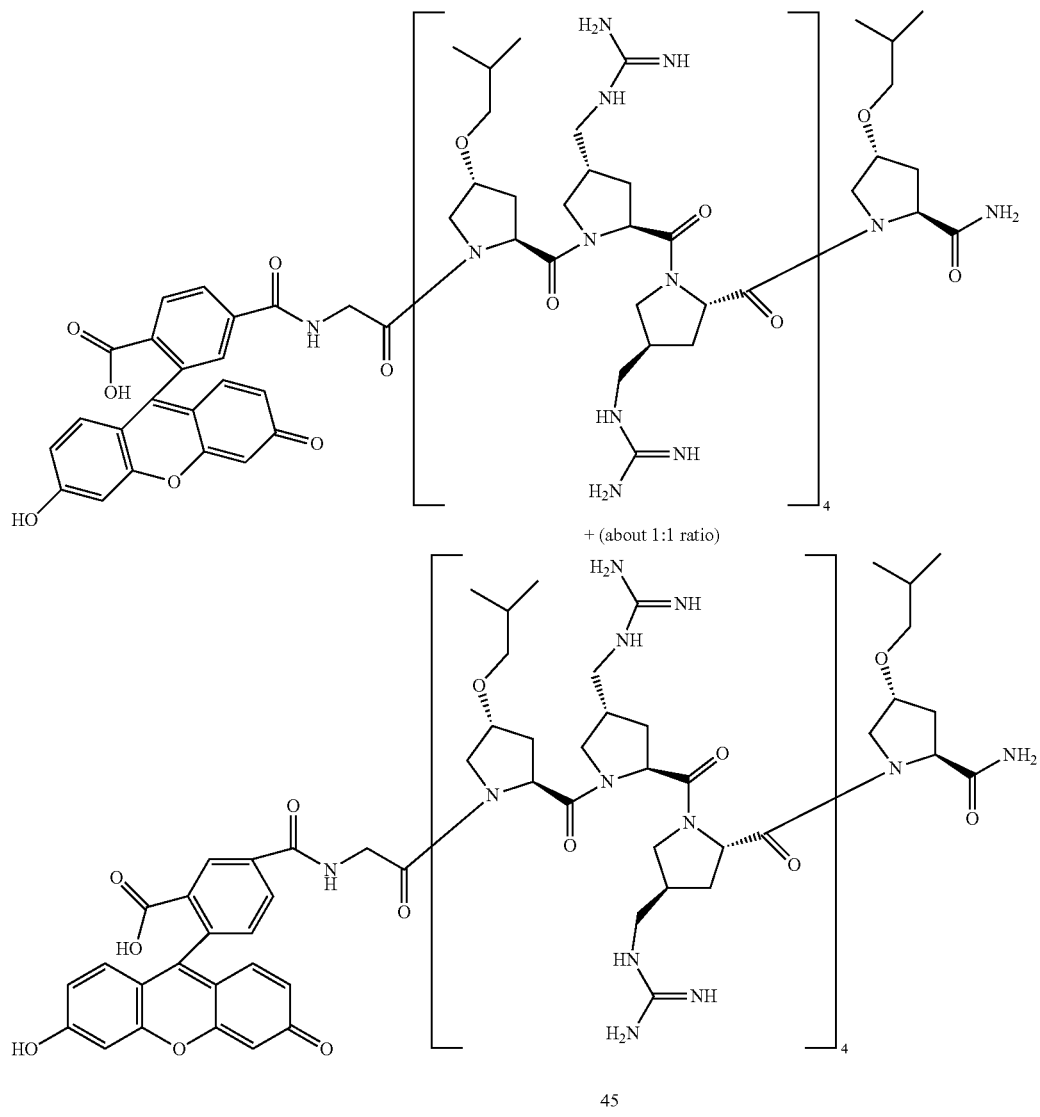
Example 2
About 1:1 Mixture Originated from the about 1:1 Mixture of 5-(and 6-)Carboxyfluorescein
Scheme 2 Provides the Synthetic Route for Preparing Compound 12
Scheme 2. Synthesis of amino acid monomer-Fmoc-PR$_{Cl}$ (Compound 12)
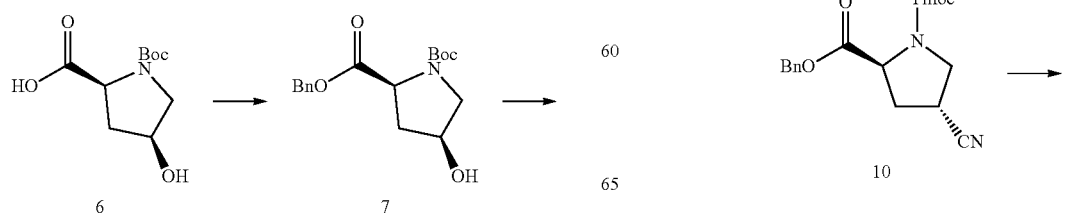
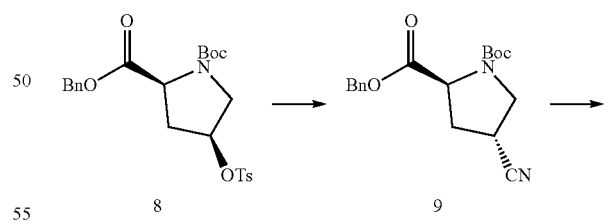

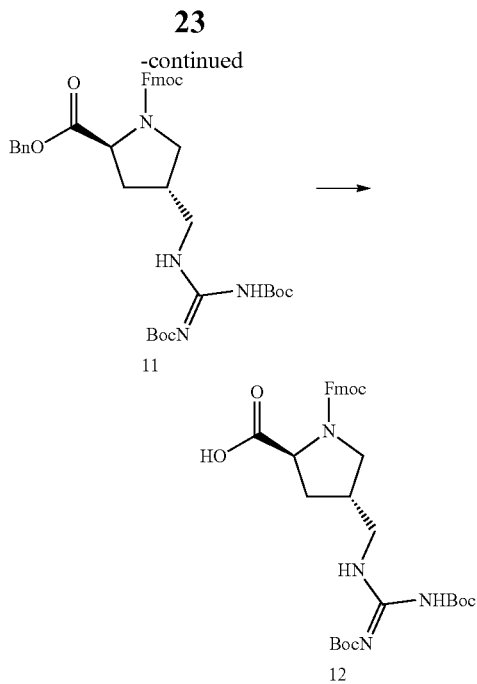

Synthesis of Compound 7

A flamed dried 1000 mL rb flask under $N_2$ (g) was charged with a magnetic stir bar, cis-N-boc-hydroxyproline, compound 6 (5.00 g, 21.6 mmol) and dry THF (430 mL). The flask was placed on an ice bath and to this stirring solution was added benzylbromide (3.35 mL, 28.1 mmol) and trimethylamine (3.91 mL, 28.1 mmol) dropwise. The reaction was allowed to warm up to room temperature and stirred for 24 hr. At this time, solvent was removed by rotary evaporation and the residue was dissolved in DCM (400 mL), washed with 10% HCl (200 mL), water (200 mL), sat. $NaHCO_3$ (200 mL) and brine (200 mL). The organic layer was then dried ($MgSO_4$, anhydrous), filtered and concentrated by rotary evaporation. The residue was dissolved in minimal DCM and purified by flash chromatography (silica gel, 5% MeOH/DCM) to yield Compound 7 as a colorless oil (5. 90 g, 18.3 mmol). $R_f$=0.65 in 10% MeOH/DCM. $^1$H NMR (CDCl3, 400 MHz): δ 7.35 (m, 5H), 5.36 (m, 1H), 5.32 (m, 1H), 5.56 (m, 2H), 3.15 (br, 1H), 2.30 (m, 1H), 2.07 (dt, J=16 Hz, 4 Hz, 1H), 1.39 (s, 9H).

Synthesis of Compound 8

A flame dried 200 mL rb flask under $N_2$(g) was charged with a magnetic stir bar, Compound 7 (4.25 g, 13.2 mmol) and dry DCM (50 mL). The flask was placed on an ice bath and to this stirring solution was added trimethylamine (3.70 mL, 26.4 mmol) followed by addition of tosyl chloride (3.77 g, 19.8 mmol) in portions over 30 min. (on smaller scales I usually add TsCl all at once). Reaction was allowed to warm up to room temperature and stirred for 24 hr. At this time the reaction was diluted with DCM (150 mL), washed with water (2×75 mL), dried ($MgSO_4$, anhydrous), filtered and concentrated. The residue was dissolved in a minimal amount of DCM and purified by flash chromatography (35% EtOAc/Hexanes) to yield Compound 8 as a colorless oil (5.02 g, 10.6 mmol, 80% yield). $R_f$=0.3 in 35% EtOAc/Hexanes. $^1$H NMR (CDCl3, 400 MHz): δ 7.70 (d, J=12, 2H), 7.31 (m, 7H), 5.10 (m, 2H), 5.08 (m, 1H), 4.42 (t, J=6 Hz, 1H), 3.65 (d, J=6 Hz, d, 1H), 3.57 (td, J=14 Hz, 4 Hz, 1H), 2.44 (m, 1H), 2.42 (s, 3H), 2.35 (q, J=4 Hz, 1H), 1.35 (s, 9H).

Synthesis of Compound 9

A flame dried 2-neck round-bottom flask was equipped with a reflux condenser and charged with a magenetic stir bar and Compound 8 (4.70 g, 9.99 mmol). The reaction flask was purged with $N_2$ (g) and DMSO (67 mL) was added. To this stirring solution was added KCN (0.976 g, 15.0 mmol) and the reaction was heated to 60° C. for 4 hrs. After allowing to cool to room temperature, the reaction was diluted with EtOAc (150 mL) and washed with water (2×75 mL) and brine (75 mL). The organic layer was dried ($MgSO_4$, anhydrous), filtered and concentrated. The residue was dissolved in minimal amount of DCM and purified by flash chromatography (20% EtOAc/Hexanes) to yield Compound 9 as a white solid (2.15 g, 6.49 mmol, 65% yield). $R_f$=0.30 in 20% EtOAc/Hexanes. $^1$H NMR (CDCl3, 400 MHz): δ 7.35 (m, 5 H), 5.17 (m, 2H), 4.47 (m, 1H), 3.89 (m, 1H), 3.65 (m, 1H), 3.21 (quint, J=8 Hz, 1H), 2.52 (m, 1H), 2.34 (m, 1H), 1.40 (s, 9H).

Synthesis of Compound 10

Compound 9 (1.90 g, 5.75 mmol) was dissolved in TFA:DCM (1:1, v/v, 65 mL) and stirred for 30 min. Solvent was removed by rotary evaporation and the residue was dissolved in 1:1 dioxane: sat. $NaHCO_3$ (130 mL total). FmocOSu (2.52 g, 7.48 mmol) was added and the reaction was stirred overnight. The reaction solution was extracted with EtOAc (3×200 mL) and the combined organic layers were dried ($MgSO_4$, anhydrous), filtered and concentrated. The residue was dissolved in minimal DCM and purified by flash chromatography (35% EtOAc/Hexanes) to yield Compound 10 as a colorless oil (2.35 g, 5.12 mmol, 90% yield). $R_f$=0.30 in 35% EtOAc/hexanes. $^1$H NMR (CDCl3, 400 MHz): δ 7.78 (m, 2H), 7.53 (m, 2H), 7.40 (m, 2H), 7.32 (m, 7H), 7.13 (dd, J=24 Hz, 12 Hz), 5.15 (m, 2H), 4.44 (m, 3H), 4.14 (t, J=6 Hz, 1H), 3.94 (m, 1H), 3.71 (m, 1H), 3.25 (m, 1H), 2.52 (m, 1H), 2.38 (m, 1H).

Synthesis of Compound 11

A flame dried 500 mL round-bottom flask under $N_2$(g) was charged with a magnetic stir bar, Compound 10 (2.15 g, 475 mmol), and dry MeOH (120 mL). To this stirring solution was added $CoCl_2.6H_2O$ (2.29 g, 9.62 mmol). The flask was placed on an ice bath and $NaBH_4$ (1.80 g, 47.5 mmol) was added in portions. The reaction was stirred at 0° C. for 30 min. At this time 1H-Pyrazole-N,N-di-boc-carboxamidine (5.90 g, 19.0 mmol) was added in portions and the reaction was allowed to warm up to room temperature and stirred overnight. After 12 hr the solution was filtered through a celite pad and the celite pad was rinsed with MeOH. The filtrate was diluted with an equal amount of water and MeOH was removed by rotary evaporation. The aqueous layer was extracted with EtOAc (3×100 mL), dried ($MgSO_4$, anhydrous), filtered and concentrated by rotary evaporation. The residue was dissolved in minimal DCM and purified by flash chromatography (20% EtOAc/Hexanes) to yield Compound 11 as a colorless oil (2.04 g, 2.92 mmol, 61% yield). $R_f$ 0.41 in 40% EtOAc/Hexanes. $^1$H NMR (CDCl3, 400 MHz): δ 11.49 (s, 1H), 8.45 (m, 1H), 7.76 (m, 2H), 7.56 (m, 2H), 7.38 (m, 2H), 7.30 (m, 7H), 5.14 (m, 2H), 4.42 (m, 3H), 4.13 (t, J=8 Hz, 1H), 3.84 (dt, J=9 Hz, 8 Hz, 1H), 3.48 (m, 1H), 3.25 (m, 1H), 2.64 (m, 1H), 2.15 (m, 1H), 2.04 (m, 1H), 1.50 (s, 18H). ESI-MS [MH]+ expected: 699.3388, observed 699.3384.

Synthesis of Compound 12

Compound 11 (2.01 g, 2.88 mmol) was dissolved in 1:1 EtOAc/Ethanol (30 mL) and to this stirring solution was added 10% Pd/C (0.300 g, 10 mol %). The solution was purged with $N_2$ (g) placing under $H_2$ (g). After 4 hr, the solution was filtered through a celite pad and the celite pad was rinsed with MeOH. The filtrate was concentrated and the residue was purified by flash chromatography (3% MeOH/DCM) to yield Compound 12 as a white solid (1.44 g, 2.37 mmol, 82% yield). $R_f$=0.47 in 10% MeOH/DCM. $^1$H NMR (CDCl3, 400 MHz): δ 11.51 (br, 1H), 8.47 (m, 1H), 7.72 (d, J=8 Hz, d, 2H), 7.56 (m, 2H), 7.38 (m, 2H), 7.30 (m, 2H), 4.39 (m, 3H), 4.19 (t, J=8 Hz, 1H), 3.75 (m, 1 Hz), 3.48 (m, 2H), 3.18 (quint, J=8 Hz), 2.63 (m, 1H), 2.28 (m, 1H), 2.00 (m, 1H), 1.49 (br, 18H) ESI-MS [MH]+ expected: 609.2919, observed: 609.2923.

Synthesis of Example 2

Peptide Synthesis: To a 10 mL peptide synthesis flask was added 50 mg of Rink-Amide ChemMatrix resin (0.24 mmol/g loading). The resin was washed with dimethylformamide (DMF) (2×, about 4 mL each). In a 13×100 mm culture tube amino acid, Compound 12 (24.6 mg, 0.06 mmol) was activated with hexafluorophosphate azabenzotriazole tetramethyl uronium (HATU) (22.8 mg, 0.06 mmol) and diisopropylethylamine (DIEA) (20.9 µL, 0.12 mmol) in DMF (4 mL) with sonication for 10 min. The resulting solution was added to the peptide synthesis flask, and the flask was agitated for 4 h. The solution was drained from the synthesis flask and the resin was washed sequentially with DMF, DCM, MeOH, DCM and DMF (2×, about 4 mL each). Piperidine in DMF (20%, 4 mL) was added to the reaction flask, and the flask was agitated for 30 min. The piperidine was drained and the resin was washed sequentially with DMF, DCM, MeOH, DCM and DMF (2×, about 4 mL each). Next, Fmoc-GAP(Boc)$_2$ (35.7 mg, 0.06 mmol) was activated with HATU (22.8 mg, 0.06 mmol) and DIEA (20.9 µL, 0.12 mmol) in DMF (4 mL) in a 13×100 mm culture tube with sonication for 10 min. The resulting solution was added to the peptide synthesis flask, and the flask was agitated for 4 h. The solution was drained from the synthesis flask and the resin was washed sequentially with DMF, DCM, MeOH, DCM and DMF (2×, about 4 mL each). Piperidine in DMF (20%, 4 mL) was added to the reaction flask, and the flask was agitated for 30 min. The piperidine was drained and the resin was washed sequentially with DMF, DCM, MeOH, DCM and DMF (2×, about 4 mL each). This procedure was repeated to until the desired peptide sequence was synthesized. Commercially available Fmoc-glycine (21.39 mg, 0.072 mmol) was activated with HATU (27.4 mg, 0.072 mmol) and DIEA (25 µL, 0.144 mmol) in DMF (4 mL) in a 13×100 mm culture tube with sonication for 10 min. The resulting solution was added to the peptide synthesis flask, and the flask was agitated for 3 h. The solution was drained from the synthesis flask and the resin was washed sequentially with DMF, DCM, MeOH, DCM and DMF (2×, about 4 mL each). Piperidine in DMF (20%, 4 mL) was added to the reaction flask, and the flask was agitated for 30 min. The piperidine was drained and the resin was washed sequentially with DMF, DCM, MeOH, DCM and DMF (2×, about 4 mL each). Completion of deprotection and coupling reactions were confirmed for primary and secondary amines using the Kaiser and Chloranil test, respectively. Finally, when appropriate, commercially available NHS-fluorescein (12.49 mg, 0.026 mmol) dissolved in DMF (4 mL) with added DIEA (8.3 µL, 0.048 mmol) was added to the reaction flask which was protected from light with foil. The flask was agitated for 24 h. The solvent was drained from the reaction flask and the resin was washed sequentially with DMF, DCM, MeOH, DCM (2×, about 4 mL each) followed by drying under high vacuum for 2 h.

Cleavage and Purification of Peptides: About 5 mL of a TFA cocktail composed of 95% TFA, 2.5% triisopropylsilane (TIPS), and 2.5% water was added to the peptide synthesis flask. The flask was agitated for 2 h. The solution was drained into a 50 mL centrifuge tube, the resin was rinsed with 5 mL of TFA cocktail followed by 5 mL of DCM. The washes were drained into centrifuge tube containing the cleaved peptide. The solvent was removed in vacuo, the crude peptide was precipitated using cold diethyl ether (25 mL) and the tube was placed in a −80° C. freezer overnight. The precipitate was collected by centrifugation at 3500 rpm and the supernatant was decanted. The resulting precipitate was dissolved in deionized water (10 mg/mL) and purified using reverse phase high performance liquid chromatography (RP-HPLC) using a C18 semi preparative column. The eluent was composed of solvent A (acetonitrile with 0.1% TFA) and solvent B (water with 0.1% TFA) at a gradient of 15-70% eluent A, flow rate of 12 mL/min, and UV detection at 214 nm and 254 nm. Fractions of the desired peptide were combined, the solvent was removed in vacuo, and lyophilized to obtain the peptides. Analysis of the purity was achieved by analytical RP-HPLC using a C18 analytical column, a flow rate of 1.2 mL/min, and UV detection at 214 nm and 254 nm; a purity of >95% was obtained with retention times of 20.1 (Fl-P14GAPC1) min. The peptide product was characterized using matrix assisted laser desorption ionization—time of flight (MALDI-TOF) mass spectrometry. Mass expected (Fl-P14GAPC1): 2623, MALDI-ToF Obtained Mass: 2624 m/z.

Synthesis of Example 3

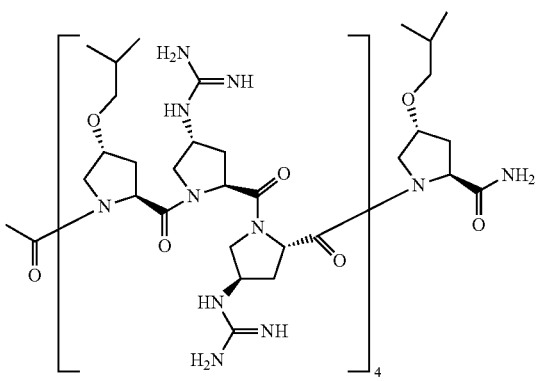

Example 3

Example 3 was prepared by the method substantially the same for making Example 1. In the peptide synthesis step, no fluorophore was added, instead the resin was treated with acetic anhydride (0.3 mL) and DIEA (0.17 mL) in DMF for 2 hours. In the cleavage and purification of peptide step, the eluent was composed of solvent A (acetonitrile with 0.1% TFA) and solvent B (water with 0.1% TFA) at a gradient of 15-65% eluent A, with retention time of 19.7 minutes. Mass expected (Ac-P13GAP): 2137, MALDI-ToF Obtained Mass: 2138 m/z.

Characterization of the Conjugates—Analytical HPLC

Purity was determined by analytical RP-HPLC using a C18 reverse phase analytical column (5 μm, 4 mm×250 mm; Phenomenex Luna) at a flow rate of 1.2 mL/min. UV detection was at 214 nm. A 30 min gradient of 15-55%, 25-55% and 30-70% solvent A (A: acetonitrile and 0.05% trifluoroacetic acid (TFA) gradient of 15-55%, 25-55% and 30-70% solvent A (A: acetonitrile and 0.05% trifluoroacetic acid (TFA); B: water and 0.05% TFA) was used.

Characterization of the Conjugates—Mass Spectrometry

Peptides were further characterized using matrix associated laser desorption ionization-time of flight (MALDI-TOF) mass spectrometry (Voyager DE, Applied Biosystems).

Method for In Vitro Antimicrobial Activity Assessment

Activities Against Pathogenic Bacteria

The minimum inhibitory concentration (MIC) of the peptides (in uM/ml) and control antibiotics (vancomycin and gentamicin) in μg/mL, were determined using the broth microdilution method according to the guidelines of the Clinical and Laboratory Standards Institute (CLSI) guidelines. See CLSI. 2007. Methods for dilution antimicrobial susceptibility tests for bacteria that grow aerobically; approved standard M7-A7. CLSI, Wayne, Pa.

TABLE 1

Comparision of MIC values [μM] for the antibacterial activity

| Strain ID | MIC (uM)/MBC | | | |
|---|---|---|---|---|
| | P14-LRR | P14-GAP (Example 1) | Vanco-mycin | Genta-micin |
| Activity against ESKAPE pathogens | | | | |
| E. faecium 700221 | 2 | 1 | >32 | >32 |
| S. aureus NRS 384 | 16 | 2 | 0.5 | 0.5 |
| K. pneumoniae 1706 | >32 | 8 | >32 | 2 |
| K. pneumonia NR 41920 | 32 | 4 | >32 | 1 |
| K. pneumonia NR 41928 | >32 | 1 | >32 | 1 |
| A. baumannii 1605 | 1 | 0.5 | 8 | >32 |
| P. aeruginosa 50573 | 16 | 2 | >32 | 0.25 |
| E. cloacae 1134 | 32 | 2 | >32 | 0.5 |
| Activity against more Staphylococcus spp. | | | | |
| S. aureus NRS 383 | 32 | 2 | 4 | >32 |
| S. aureus NRS 382 | 32 | 2 | 1 | 0.5 |
| S. aureus RN 4220 | 32 | 2 | 0.5 | 0.5 |
| S. aureus ATCC 6538 | 16 | 1 | 0.5 | 0.125 |
| S. epidermidis NRS 101 | 2 | 1 | 2 | 32 |
| VRSA 5 | 16 | 2 | 4 | 0.5 |
| VRSA 10 | 8 | 2 | >32 | 0.5 |
| Activity against more Pseudomonas aeruginosa | | | | |
| P. aeruginosa 48982 | 32 | 4 | >32 | >32 |
| P. aeruginosa 31040 | 32 | 2 | >32 | 16 |
| P. aeruginosa 31041 | 32 | 2 | >32 | 32 |
| Activity against more Acinetobacter baumannii | | | | |
| A. baumannii 1747 | 1 | 0.5 | >32 | 0.25 |
| A baumannii 19606 | 2 | 1 | 32 | 16 |
| Activity against enteric pathogens | | | | |
| L. monocytogenes 191112 | 8 | 2 | 1 | 0.5 |
| S. flexneri 1a | 4 | 1 | >32 | 0.5 |
| S. enteritidis | 4 | 1 | >32 | 0.25 |
| E. coli 21922 | 4 | 1 | >32 | 2 |
| S. typhimurium LT2 | 16 | 1 | >32 | 0.5 |

Antimicrobial activities of Example 1 (P14-GAP) and other anti-bacterial peptides, antibiotics were evaluated/compared with a series of Gram positive and negative bacteria, including a range of intracellularpathogens (Table 1). Comparing with previously disclosed antibacterial cell-penetrating peptides, the present disclosure provides novel antibacterial cell-penetrating peptides that have shorter linker between a pyrrolidine ring and a guanidine group. Such modified peptides with shorter linkers, such as Example 1, provided unexpectedly higher potency against a broader scope of bacterial. Example 1 is the compound that showed highest potency for every single bacterial. Because the activity of Example 1 came from the peptide moiety alone, the incorporation of other active moieties may provide further benefits.

Time-Kill Curves Against S. aureus MRSA US300 for Example 3

Exponential-phase S. aureus MRSA US300 was diluted in CAMHB media and challenged with the indicated test agents at concentrations representing 2× MIC (a), or 4× MIC (b). Untreated control received phosphate buffered saline (PBS). Viability was enumerated at the indicated time points by serial dilution plating. Each point represents the mean $Log_{10}$ CFU/ml +SD of triplicate determinations.

Time to kill curves were obtained with Example 3 and the known antibiotics linezolid and vancomycin against *S. aureus* MRSA US300. A greater than 5 log reduction in bacteria levels was observed with Example 3 in 2 hours at both 2- and 4-times its MIC value, whereas vancomycin took 24 hours for a similar reduction and linezolid obtained only about a log reduction in 24 hours.

Those skilled in the art will recognize that numerous modifications can be made to the specific implementations described above. The implementations should not be limited to the particular limitations described. Other implementations may be possible.

We claim:
1. A compound of Formula I:

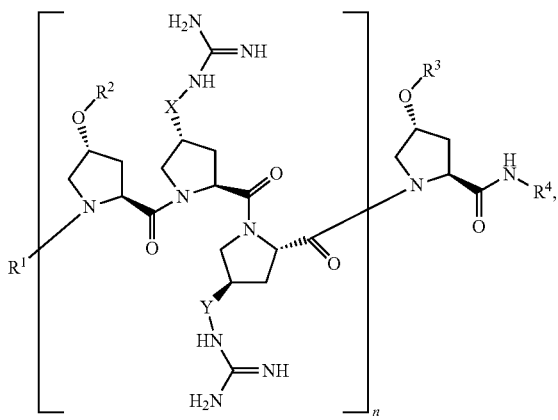

or a stereoisomer, tautomer, solvate, pharmaceutically acceptable salt, or derivative thereof,
wherein:
  $R^1$ is H, an optionally substituted straight, branched or cyclic alkyl or acyl, an optionally substituted aryl or aroyl, an optionally substituted heteroaryl or heteroaroyl, an amino acid moiety, a dye moiety, a fluorophore moiety, a pharmaceutical conjugating agent moiety, an antibiotic moiety, or

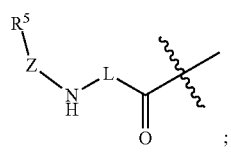

$R^2$ and $R^3$ are each independently H, a $C_1$-$C_8$ branched or unbranched alkyl chain, a $C_3$-$C_8$ cyclic alkyl, an optionally substituted aryl, or an optionally substituted heteroaryl;
  $R^4$ is H, a $C_1$-$C_8$ branched or unbranched alkyl chain, or a $C_3$-$C_8$ cyclic alkyl, an optionally substituted aryl, or an optionally substituted heteroaryl;
  $R^5$ is H, a dye moiety, a fluorophore moiety, a pharmaceutical conjugating agent moiety, or an antibiotic moiety;
  L is $C_1$-$C_8$ branched or unbranched alkyl chain, or a $C_3$-$C_8$ cyclic alkyl;
  X and Y are each independently a bond, or a $C_1$-$C_3$ linker, wherein one of the carbon of the $C_1$-$C_3$ linker is optionally replaced with a heteroatom selected from the group consisting of N, O, and S;
  Z is a bond, or a linker comprising an optionally substituted straight, branched or cyclic alkyl, an amide group, a carbonyl group, a heteroatom selected from the group consisting of N, O, and S, a disulfide bond (S—S bond), or any combination thereof; and
  n is 2-8.

2. The compound of claim 1, wherein $R^1$ and/or $R^5$ each independently represents the moiety of an aminoglycoside antibiotics or any derivative thereof.

3. The compound of claim 1, wherein $R^1$ and/or $R^5$ each independently represents an antibiotic moiety, wherein the antibiotic moiety is of an antibiotics selected from the group consisting of Gentamicin, Streptomycin, Kanamycin, Fradiomyctn, Paromomycin, Tobramycin, Netilmicin, Amikacin, Neomycin, Ribostamycin, Dibekacin, Sisomicin, Isepamicin, Bekanamycin, Astromicin, Plazomicin, Vancomycin, Linezolid, Erythromycin, Eperezolid, and any derivative thereof.

4. The compound of claim 1, wherein $R^2$ and $R^3$ are each independently $C_1$-$C_4$ branched or unbranched alkyl chain.

5. The compound of claim 1, wherein $R^2$ and $R^3$ are isobutyl group.

6. The compound of claim 1, wherein $R^4$ is hydrogen.

7. The compound of claim 1, wherein L is —($CH_2$)—.

8. The compound of claim 1, wherein $R^1$ and/or $R^5$ each independently represents an antibiotic moiety, wherein the antibiotic moiety is of an antibiotics selected from the group consisting of Gentamicin, Streptomycin, Kanamycin, Fradiomyctn, Paromomycin, Tobramycin, Netilmicin, Amikacin, Neomycin, Ribostamycin, Dibekacin, Sisomicin, Isepamicin, Bekanamycin, Astromicin, Plazomicin, Vancomycin, Linezolid, Erythromycin, Eperezolid, and any derivative thereof; wherein $R^2$ and $R^3$ are isobutyl group; $R^4$ is hydrogen; L is —($CH_2$)—; X and Y are a bond; Z is a carbonyl group; and n is 4.

9. The compound of claim 1 wherein, $R^1$ and/or $R^5$ each independently represents an aminoglycoside antibiotics moiety, and the aminoglycoside antibiotics is selected from the group consisting of Gentamicin, Kanamycin, Tobramycin, Amikacin, Neomycin, Plazomicin, and any derivative thereof; $R^2$ and $R^3$ are isobutyl group; $R^4$ is hydrogen; L is —($CH_2$)—; X and Y are a bond; Z is a carbonyl group; and n is 4.

10. The compound of claim 1, wherein the compound is:
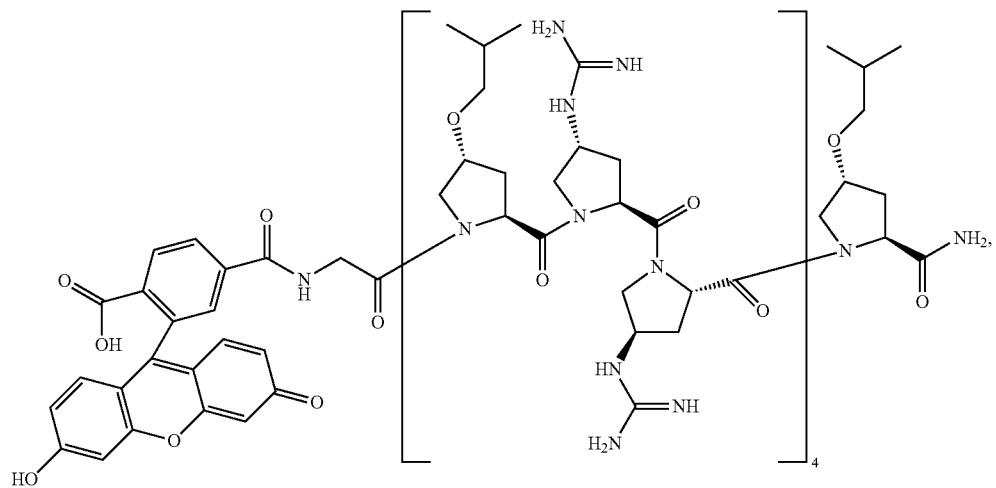
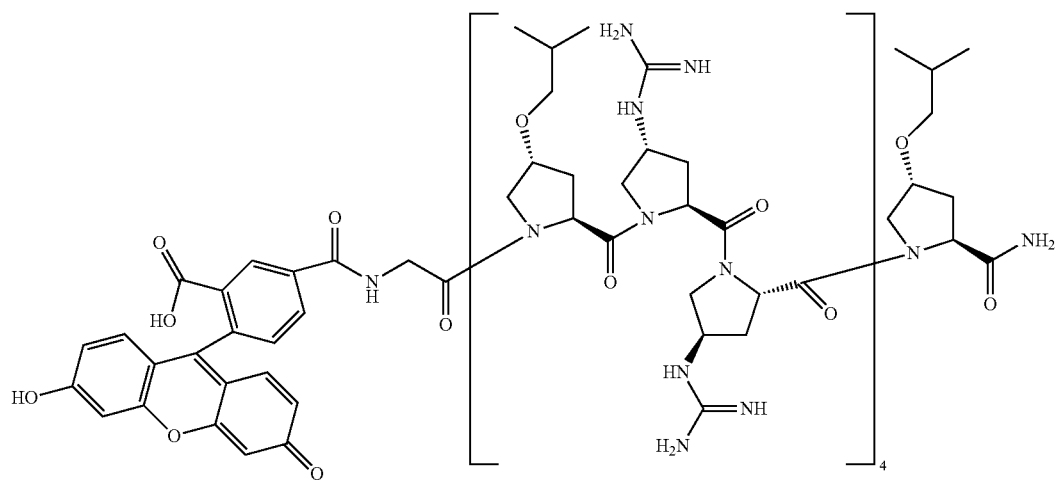
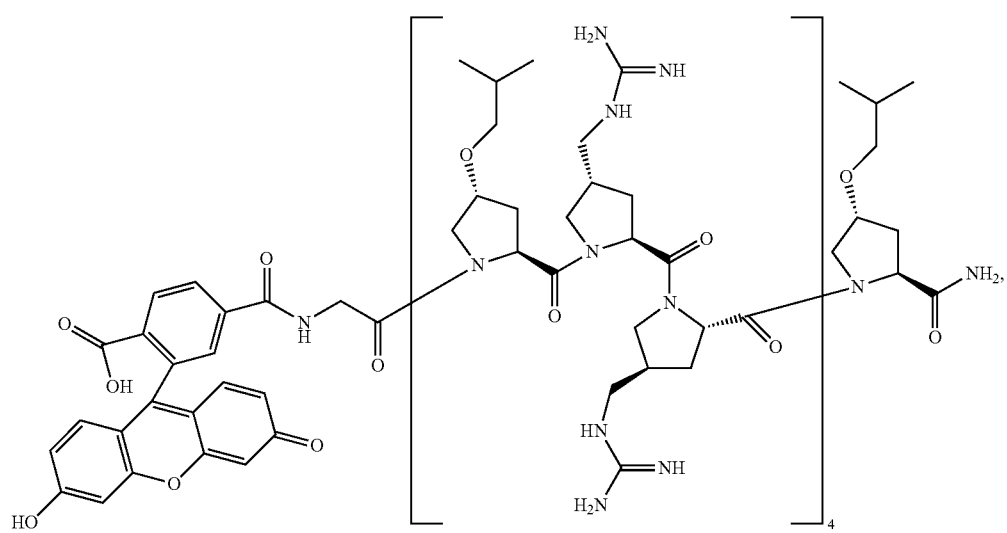

-continued

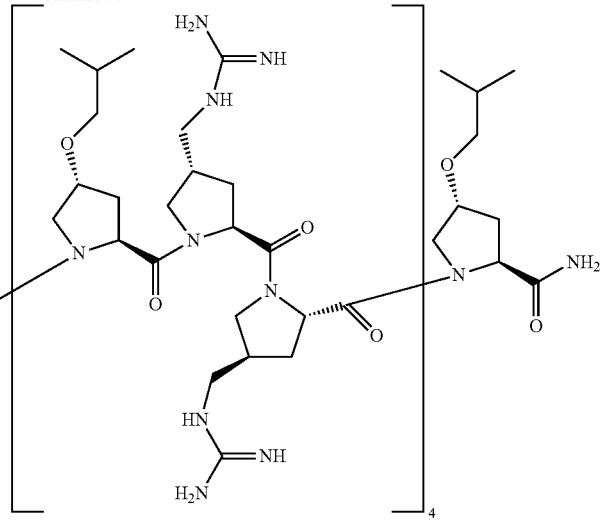

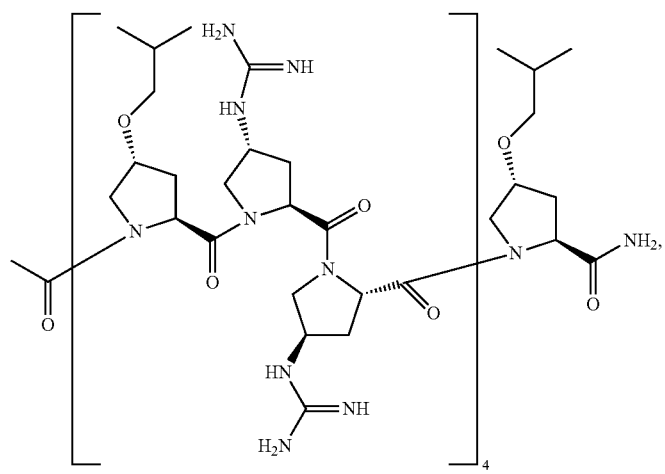

or a stereoisomer, tautomer, solvate, pharmaceutically acceptable salt, or derivative thereof.

11. A method for treating a subject in need thereof, having a bacterial biofilm infection with an effective amount of compound of claim 1, or a stereoisomer, tautomer, solvate, pharmaceutically acceptable salt, or derivative thereof.

12. The method of claim 11, wherein the compound of claim 1 inhibits the formation of a biofilm.

13. The method of claim 11, wherein the compound of claim 1 inhibits the growth of an established biofilm.

14. The method of claim 11, wherein the compound of claim 1 is anti-inflammatory.

15. The method of claim 11, wherein the compound of claim 1 is:

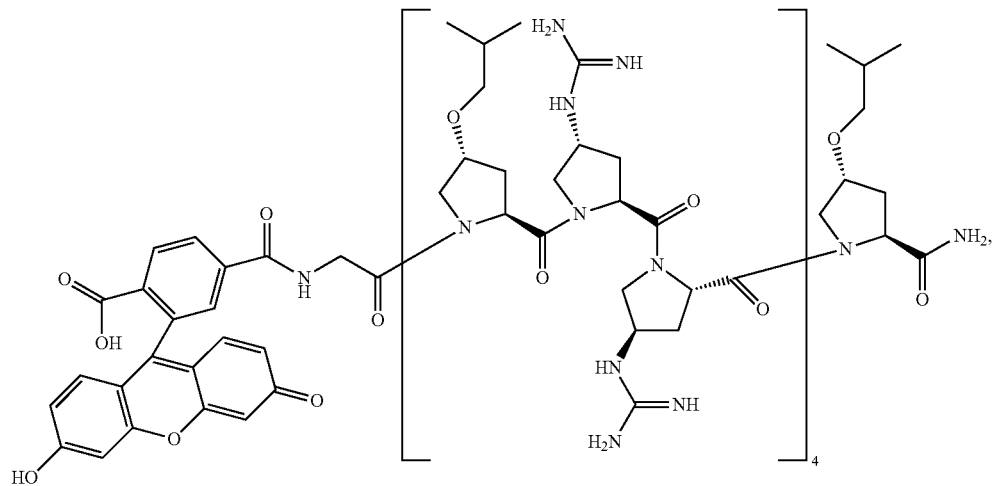
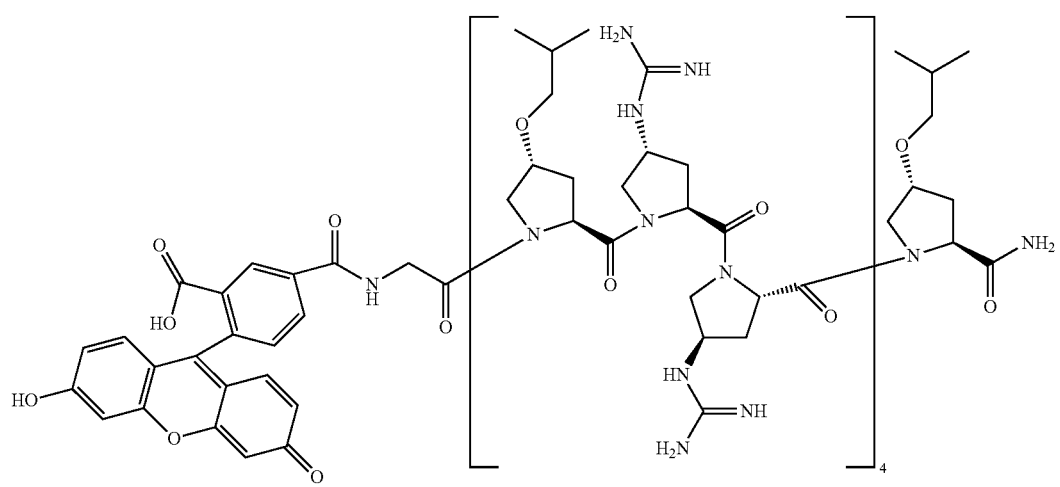
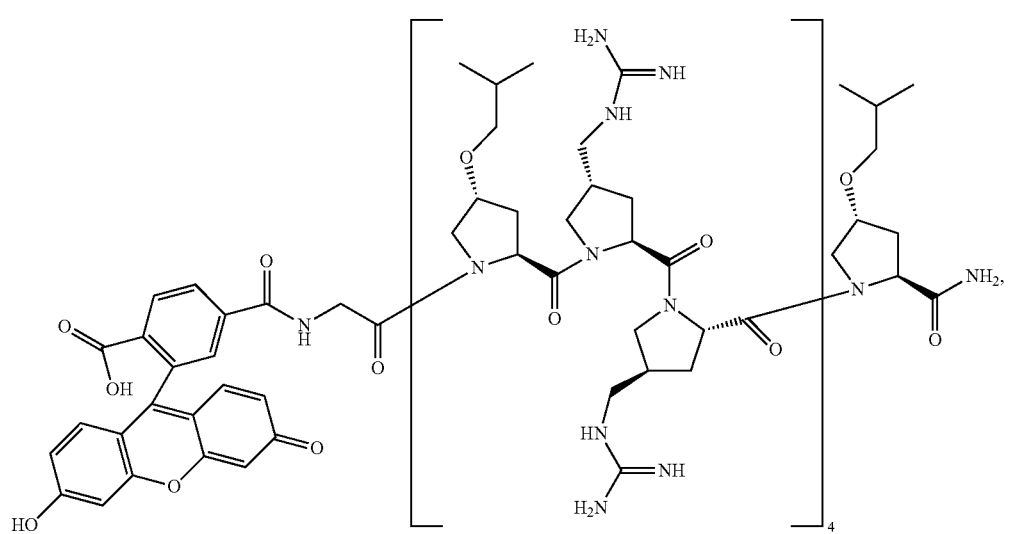

-continued
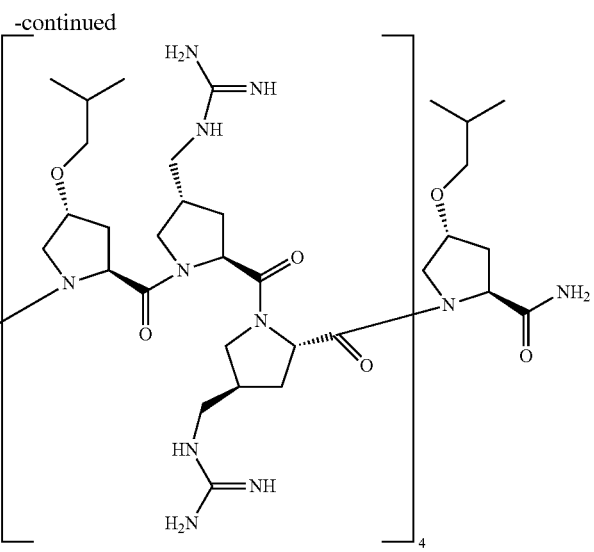
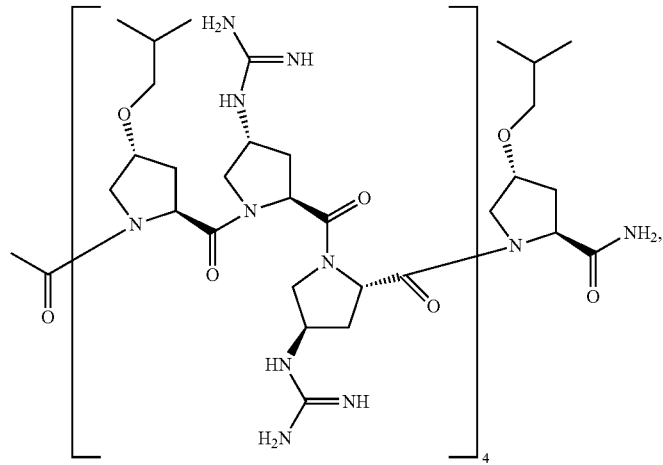
or a stereoisomer, tautomer, solvate, pharmaceutically acceptable salt, or derivative thereof.
* * * * *